United States Patent
Bohlin et al.

[11] Patent Number: 6,162,816
[45] Date of Patent: Dec. 19, 2000

[54] CRYSTALLINE FORM OF THE S-ENANTIOMER OF OMEPRAZOLE

[75] Inventors: Martin Bohlin, Johanneshov; Karol Horvath, Södertälje, both of Sweden

[73] Assignee: AstraZeneca AB, Sodertalje, Sweden

[21] Appl. No.: 09/000,154

[22] PCT Filed: Dec. 16, 1997

[86] PCT No.: PCT/SE97/02125

§ 371 Date: Jan. 28, 1999

§ 102(e) Date: Jan. 28, 1999

[87] PCT Pub. No.: WO98/28294

PCT Pub. Date: Jul. 2, 1998

[30] Foreign Application Priority Data

Dec. 20, 1996 [SE] Sweden ................................ 9604793

[51] Int. Cl.$^7$ .................. A61K 31/44; C07D 401/12
[52] U.S. Cl. ........................ 514/338; 546/273.7
[58] Field of Search .................. 514/338; 546/273.7

[56] References Cited

U.S. PATENT DOCUMENTS

| | | | |
|---|---|---|---|
| 4,255,431 | 3/1981 | Junggren et al. | 514/338 |
| 4,738,974 | 4/1988 | Brändström | 514/338 |
| 4,786,505 | 11/1988 | Lovgren et al. | 424/468 |
| 5,693,818 | 12/1997 | von Unge | 546/272.7 |
| 5,714,504 | 2/1998 | Lindberg et al. | 514/338 |
| 5,817,338 | 10/1998 | Bergstrand et al. | 424/468 |
| 5,877,192 | 3/1999 | Lindberg et al. | 514/338 |
| 5,900,424 | 5/1999 | Källström et al. | 514/338 |

FOREIGN PATENT DOCUMENTS

| | | |
|---|---|---|
| 0005129 | 10/1979 | European Pat. Off. . |
| 0124495 | 11/1984 | European Pat. Off. . |
| 0247983 | 12/1987 | European Pat. Off. . |
| WO 92/08716 | 5/1992 | WIPO ............... 546/273.7 |
| WO 94/27988 | 12/1994 | WIPO ............... 514/338 |
| 9501977 | 1/1995 | WIPO . |
| 9601623 | 1/1996 | WIPO . |

OTHER PUBLICATIONS

The Merck Index, Eleventh Edition, p. 1082, Ref. No. 6800, 1989.

Per Erlundsson, Journal of Chromatograhy, vol. 532, pp. 305–319, 1990.

von Unge, S. et al. "Stereochemical assignment of the enantiomers of omeprazole from X–ray analysis of a fenchyloxylmethyl derivative of (+)–(R)–omeprazole", *Tetrahedron Asymmetry*, vol. 8, No. 12, pp. 1967–1970 (1997).

*Primary Examiner*—Alan L. Rotman
*Attorney, Agent, or Firm*—White & Case LLP

[57] ABSTRACT

The invention provides S-omeprazole in a neutral form characterised in that it is in a solid state, preferably in a partly crystalline or substantially crystalline state, such as form A or form B. Furthermore, the invention provides processes for the preparation of S-omeprazole and its use in medicine.

17 Claims, 2 Drawing Sheets

CRYSTALLINE FORM OF THE S-ENANTIOMER OF OMEPRAZOLE

This application is a 371 of PCT/SE97/02125 filed Dec. 12, 1997.

FIELD OF THE INVENTION

The invention provides a neutral form of the S-enantiomer of omeprazole which is S-5-methoxy-2-[[(4-methoxy-3,5-dimethyl-2-pyridinyl)-methyl]sulfinyl]-1H-benzimidazole in a new physical form, more specifically in a solid state which can be at least partly crystalline, processes for preparing such a form of the S-enantiomer of omeprazole and pharmaceutical compositions containing it.

BACKGROUND OF THE INVENTION

The compound 5-methoxy-2-[[(4-methoxy-3,5-dimethyl-2-pyridinyl)methyl]sulfinyl]-1H-benzimidazole, having the generic name omeprazole, and therapeutically acceptable salts thereof, are described in EP 5129. The specific alkaline salts of omeprazole are disclosed in EP 124 495. Omeprazole is effective as a gastric acid secretion inhibitor, and is useful as an antiulcer agent. In a more general sense, omeprazole may be used for prevention and treatment of gastric-acid related diseases in mammals and especially in man.

Omeprazole is a sulfoxide and a chiral compound, wherein the sulfur atom being the stereogenic center. Thus, omeprazole is a racemic mixture of its two single enantiomers, the R-omeprazole and the S-omeprazole. The absolute configurations of the enantiomers of omeprazole have been determined by an X-ray study of an N akylated derivative of the (+)-enantiomer in neutral form. The (+)-enantiomer of the neutral form and the (−)-enantiomer of the neutral form were found to have the R and S configuration, respectively. The conditions for the optical rotation measurement for each of these enantiomers are described in WO 94/27988.

WO 92/08716 discloses R-omeprazole in its neutral form as an amorphous solid in Example 6. Different salts of the single enantiomers of omeprazole are described in WO 94/27988. The latter document discloses the preparation of the neutral form of the S-enantiomer of omeprazole in, for example, Example 10. However, it was obtained in the form of a syrup or oil which is unsuitable for pharmaceutical use because of the difficulty of handling an oil and incorporating it into solid pharmaceutical compositions, especially in a reproducible manner.

DESCRIPTION OF THE INVENTION

According to the invention there is provided S-omeprazole in a neutral form, i.e. not in the form of a salt, characterised in that the S-omeprazole is in a solid state.

Neutral S-omeprazole according to the invention is advantageous because it is more stable, easier to handle and store. It is also easier to characterise because it exists in a more well defined state, easier to purify and easier to synthesise in a reproducible manner.

S-Omeprazole according to the invention can in general be in an amorphous, partly crystalline or substantially crystalline solid state. Preferably it is in a partly crystalline solid state or a substantially crystalline solid state. More preferably it is in either of form A which is a crystalline form or form B which is a less crystalline form.

DETAILED DESCRIPTION OF THE DRAWINGS

DETAILED DESCRIPTION OF THE INVENTION

Forms A and B of S-omeprazole in neutral form are characterised by having X-ray powder diffraction patterns having the 20 degree angles, d-values and relative intensities given in Table 1.

TABLE 1

| Form A | | | Form B | | |
|---|---|---|---|---|---|
| Angle °2θ | d-value, α¹ (Å) | Relative Intensity | Angle °2θ | d-value, α¹ (Å) | Relative Intensity |
| 5.78 | 15.29 | Very strong | 5.65 | 15.64 | Strong |
| 9.50 | 9.30 | Weak | 9.57 | 9.23 | Medium |
| 9.99 | 8.85 | Weak | 13.75 | 6.44 | Medium |
| 11.54 | 7.66 | Weak | 15.75 | 5.62 | Medium |
| 12.54 | 7.05 | Weak | 16.47 | 5.38 | Medium |
| 16.27 | 5.44 | Strong | 19.36 | 4.58 | Weak |
| 17.09 | 5.19 | Strong | 21.94 | 4.05 | Weak |
| 18.18 | 4.88 | Weak | 24.69 | 3.60 | Weak |
| 18.95 | 4.68 | Strong | 25.28 | 3.52 | Weak |
| 20.90 | 4.25 | Medium | 27.33 | 3.26 | Weak |
| 21.57 | 4.12 | Medium | 29.75 | 3.00 | Very Weak |
| 22.29 | 3.99 | Medium | | | |
| 23.17 | 3.84 | Weak | | | |
| 25.22 | 3.53 | Very Weak | | | |
| 25.90 | 3.44 | Weak | | | |
| 26.45 | 3.37 | Weak | | | |
| 27.70 | 3.22 | Very Weak | | | |
| 29.66 | 3.01 | Very Weak | | | |

Figure 1:
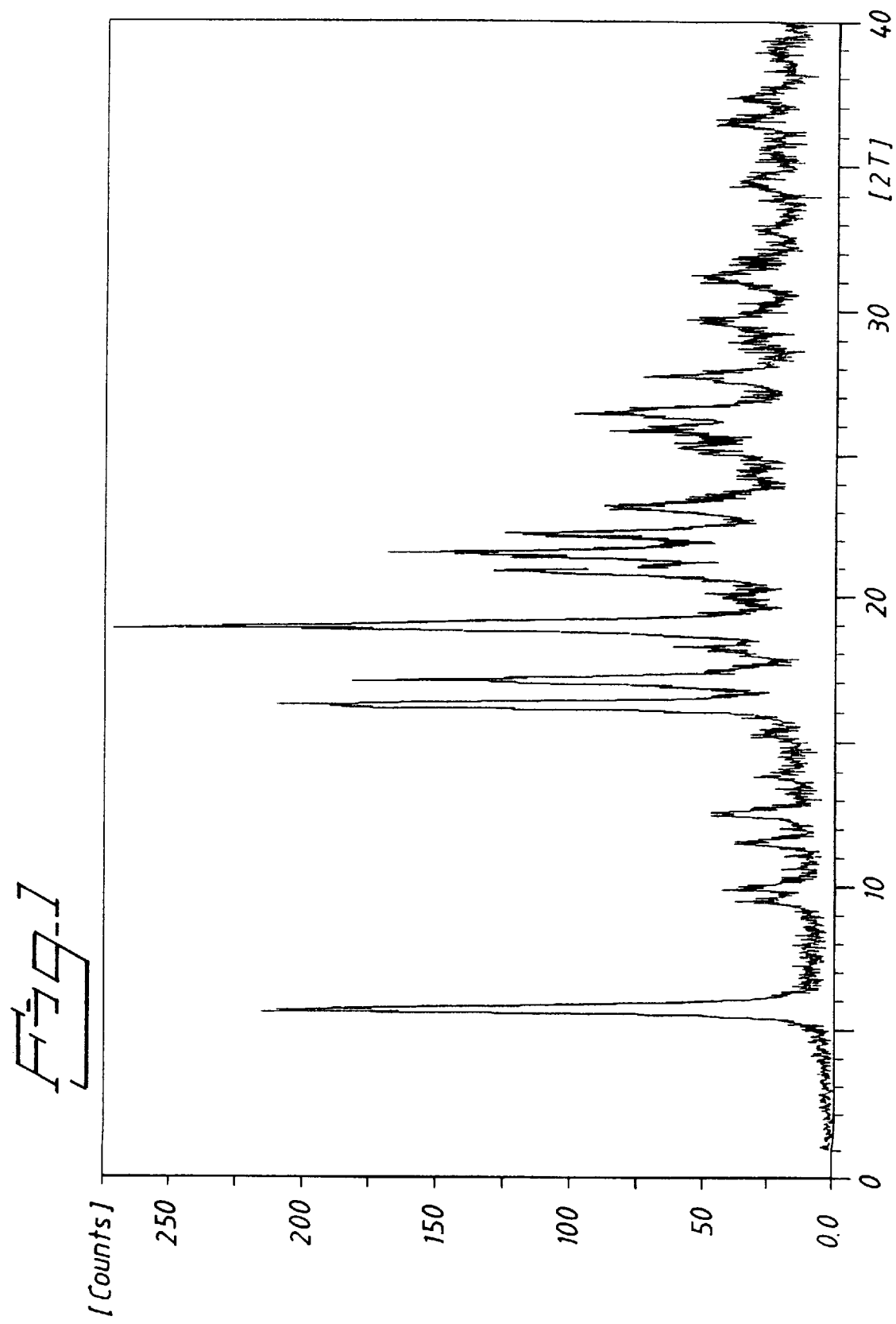
FIG. 1 shows the X-ray powder diffraction pattern of neutral S-omeprazole in form A.
Figure 2:
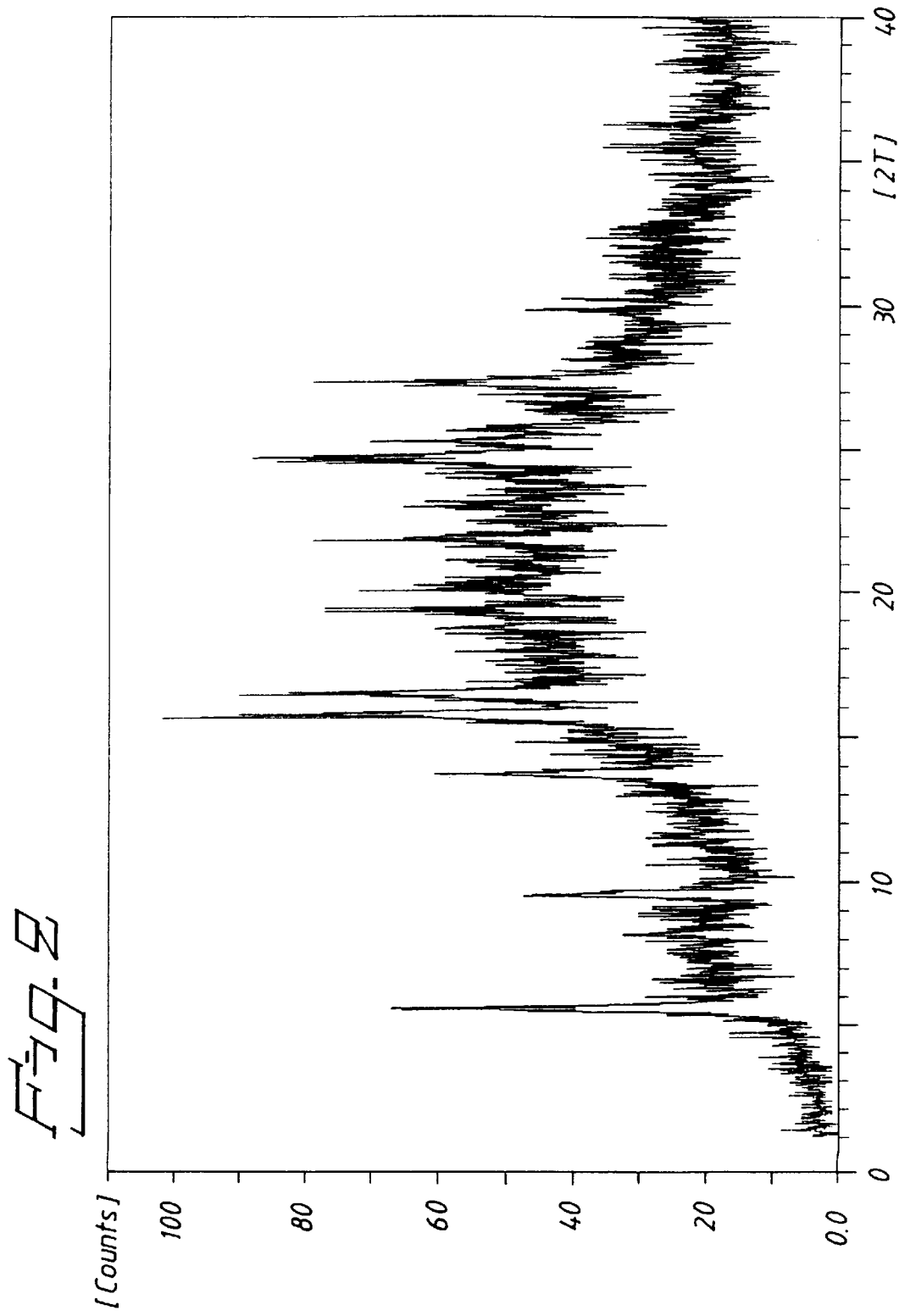
FIG. 2 shows the X-ray powder diffraction pattern of neutral S-omeprazole in form B.

More particularly, neutral S-omeprazole in form A is characterised by the X-ray powder diffraction pattern given in FIG. 1 and neutral S-omeprazole in form B is characterised by the X-ray powder diffraction pattern given in FIG. 2. The X-ray powder diffraction (XRD) patterns in these were obtained in Bragg-Bretano geometry. Since form B is less crystalline and also has peaks in its powder diffractogram which are related to peaks in the diffractogram of form A it is not clear that this is a different crystal form.

The X-ray diffraction analysis was performed according to standard methods, which can be found in e.g. Kitaigorodsky, A. I. (1973), Molecular Crystals and Molecules, Academic Press, New York;Bunn, C. W. (1948), Chemical Crystallography, Clarendon Press, London;or Klug, H. P. & Alexander, L. E. (1974), X-Ray Diffraction Procedures, John Wiley & Sons, New York.

The expression S-omeprazole refers to the fact that it is substantially free of the R-enantiomer, preferably with an enantiomeric excess of 90%, and more preferably 95% e.e.

In a further aspect, the invention relates to processes for the preparation of neutral S-omeprazole in a solid state which comprise (a) evaporating a solution of neutral S-omeprazole in one or more organic solvents to a highly concentrated solution, adding a further solvent to the highly concentrated solution and evaporating further until solid amorphous neutral S-omeprazole is formed; or (b) crystallization from a solution of S-omeprazole in one or more organic solvents and optionally water; or (c) precipitation from a solution of an alkaline salt of S-omeprazole in water and, optionally one or more organic solvents, with a suitable acid.

Process (a) might be further defined by the following aspects. The highly concentrated solution formed in process (a) should not be so concentrated that it is not possible to carry out the second half of the process. After the further evaporation, additional amounts of a further solvent, i.e. a second solvent, may optionally be added and the remaining solvent is evaporated until no more solvent can be removed. This further solvent is preferably one in which neutral S-omeprazole is soluble, but not very soluble, and is more preferably an anti-solvent. The repeated evaporation procedure helps to remove all the initial solvent which otherwise would prevent the formation of a solid substance. The resulting amorphous precipitate may optionally be further dried, for instance under reduced pressure.

More particularly process (a) may be carried out by dissolving a water soluble salt of S-omeprazole, preferably by using an alkali metal salt (e.g. the potassium or preferably sodium salt) in water and extracting neutral S-omeprazole to a water immiscible solvent or water immiscible solvent mixture (e.g. methylene chloride or toluene, preferably methylene chloride), by decreasing the pH in the water phase, e.g. from about 11, preferably to a pH of from 7 to 10 (e.g. to a pH of from 7 to 8) with a water soluble acid (e.g. aqueous HCl or aqueous acetic acid, preferably diluted acetic acid). The organic phase containing the neutral form of S-omeprazole may be separated from the water phase and solvent evaporated until a highly concentrated solution is formed, preferably leaving 1–2 ml solvent/g of S-omeprazole. A first portion of a further solvent, e.g iso-octane or n-heptane, is added in an amount of, for example, 5–10 m/g of S-omeprazole. More solvent is evaporated from the resulting mixture until solid amorphous neutral S-omeprazole is formed. Further amounts of a further solvent, e.g. 5–10 ml/g of S-omeprazole, may be added and re-evaporated until no more solvent can be removed. The resulting solid amorphous neutral S-omeprazole may optionally be further dried, for instance under reduced pressure.

Process (b) might be further defined by the following aspects. The solution of neutral S-omeprazole used in the process (b) of the invention can be formed either (i) by dissolution of already isolated neutral S-omeprazole, for instance from process (a) or (ii) it can be the result of a previous step where neutral S-omeprazole is formed by chemical reaction, or (iii) it can be a solution formed by extraction.

Crystallization in process (b) may be induced by decreasing the solubility of S-omeprazole, e.g. by cooling the mixture, by evaporation of some of the solvents or by mixing with, e.g. by adding, some precipitating solvent or anti-solvent. The crystallization may start spontaneously, but it is preferable to add seeds of the desired form of neutral S-omeprazole. Most preferably seeds of S-omeprazole form A are added.

Suitable solvents, in which neutral S-omeprazole is soluble but not very soluble and which are preferably used for preparing solutions for use in process (b) by dissolution of neutral S-omeprazole, are, for example, ethyl acetate, iso-butanol, isopropanol, methyl isobutyl ketone, acetone, and acetonitrile. Preferably the solvent is ethyl acetate or acetonitrile; most preferably it is ethyl acetate. The preferred amount of organic solvent is 4–10 ml/g of S-omeprazole.

Suitable organic solvents in which neutral S-omeprazole is very soluble which are suitable for use when the solution in process (b) is a reaction solution or obtained by extraction, are, for example, methylene chloride and toluene. Since neutral S-omeprazole is very soluble in these solvents, it can be necessary to use an anti-solvent to induce crystallisation.

A suitable anti-solvent is, for example, iso-octane, acetonitrile or ethyl acetate; preferably it is ethyl acetate or isooctane. Preferably the crystallisation is induced by adding seed crystals, in particular crystals of form A.

Process (c) might be further defined as described below. Process (c) according to the invention is preferably carried out by dissolving a water soluble salt of S-omeprazole in water or a mixture of water and an organic solvent and crystallisation is induced by mixing with, e.g by addition of, a solution of an acid such that the pH of the final solution is still high enough to prevent significant degradation of the product. The organic solvent(s) is preferably a water miscible solvent(s) such as for instance, acetone, acetonitrile or a lower alkyl alcohol. The acid may be, for example, HCl or acetic acid, preferably aqueous acetic acid. The pH of the final solution may be, for example, from 7 to 10, preferably from 7 to 8.

The starting material of process (c) of the invention is preferably a water soluble salt of S-omeprazole, for example an alkali metal salt, particularly a sodium salt. The resulting precipitate of neutral S-omeprazole is generally in a partly crystalline solid state, in particular, in form B.

Evaporation of solvents is preferably carried out by vacuum evaporation using, for example a pressure of from 10 to 20 mbar. Mixing, e.g. agitation, is preferable during crystallization. The crystallization should continue for a period to ensure that crystallization is as complete as possible, e.g. from 1–15 hours.

When the neutral S-omeprazole is crystallized, as in processes (b) and (c), the crystals may be separated from the solution, e.g. by filtration or centrifugation, followed by washing with a washing liquid, preferably a solvent mixture in which the particular form of neutral S-omeprazole has a very low solubility, for example, an anti-solvent. The preferred proportion of washing liquid to product is from 1:1 to 5:1 by weight. The separated neutral S-omeprazole crystals are preferably dried under conditions which avoid degradation of the product, e.g at +30 to +40° C., preferably at reduced pressure of e.g. 10 to 20 mbar, for e.g. 10 to 48 hours.

Neutral S-omeprazole according to the invention is effective as a gastric acid secretion inhibitor, and is useful as an antiulcer agent. In a more general sense, it can be used for prevention and treatment of gastric-acid related conditions in mammals and especially in man, including e.g. reflux esophagitis, gastritis, duodenitis, gastric ulcer and duodenal ulcer. Furthermore, it may be used for treatment of other gastrointestinal disorders where gastric acid inhibitory effect is desirable e.g. in patients on NSAID therapy, in patients with Non Ulcer Dyspepsia, in patients with symptomatic gastro-esophageal reflux disease, and in patients with gastrinomas. Neutral S-omeprazole according to the invention may also be used in patients in intensive care situations, in patients with acute upper gastrointestinal bleeding, pre- and postoperatively to prevent aspiration of gastric acid and to prevent and treat stress ulceration. Further, neutral S-omeprazole may be useful in the treatment of psoriasis as well as in the treatment of Helicobacter infections and diseases related to these.

Any suitable route of administration may be employed for providing the patient with an effective dosage of neutral S-omeprazole according to the invention. For example, peroral or parental formulations and the like may be employed. Dosage forms include capsules, tablets, dispersions, suspensions and the like.

According to the invention there is further provided a pharmaceutical composition comprising neutral S-omeprazole according to the invention, as active ingredient, in association with a pharmaceutically acceptable carrier, diluent or excipient and optionally other therapeutic ingredients. Compositions comprising other therapeutic ingredients are especially of interest in the treatment of Helicobacter infections. The invention also provides the use of neutral S-omeprazole according to the invention in the manufacture of a medicament for use in the treatment of a gastric-acid related condition and a method of treating a gastric-acid related condition which method comprises administering to a subject suffering from a said condition a therapeutically effective amount of neutral S-omeprazole according to the invention.

The compositions of the invention include compositions suitable for peroral or parental administration. The most preferred route is the oral route. The compositions may be conveniently presented in unit dosage forms, and prepared by any methods known in the art of pharmacy, such as tablets, capsules and multiple unit tablets.

The most suitable route of administration as well as the magnitude of a therapeutic dose of neutral S-omeprazole according to the invention in any given case will depend on the nature and severity of the disease to be treated. The dose, and dose frequency, may also vary according to the age, body weight, and response of the individual patient. Special requirements may be needed for patients having Zollinger-Ellison syndrom, such as a need for higher doses than the average patient. Children and patients with liver diseases generally will benefit from doses that are somewhat lower than the average. Thus, in some conditions it may be necessary to use doses outside the ranges stated below. Such higher and lower doses are within the scope of the present invention.

In general, a suitable oral dosage form may cover a dose range from 10 mg to 80 mg total daily dose, administered in one single dose or equally divided doses. A preferred dosage range is from 20 mg to 60 mg and, especially preferred from 20 mg to 40 mg total daily Neutral S-omeprazole according to the invention may be combined as the active component in intimate admixture with a pharmaceutical carrier according to conventional techniques, such as the oral formulations described in WO 96/ 01623 and EP 247 983, the disclosures of which are hereby incorporated as a whole by reference.

The invention is illustrated by the following examples which should not be interpreted as limiting the invention. The best mode to carry out the invention is according to one of the examples giving S-omeprazole form A.

EXAMPLE 1

Sodium salt of S-omeprazole (8 g) was dissolved in water (80 ml) at room temperature. Methylene chloride (80 ml) was added and the product was extracted to the organic phase by addition of diluted (4.8 ml, 25% v/v) acetic acid. The mixture was stirred for 5 minutes and then the two phases were allowed to separate. The organic phase was separated off and charged into a round flask. The methylene chloride was evaporated under vacuum until a highly concentrated solution containing approximately 1 ml of methylene chloride per 1 g of omeprazole was formed. Iso-octane (40 ml) was added and the solvent was evaporated again until an almost dry, amorphous substance was formed. A further amount of iso-octane was added (20 ml) and the slurry was concentrated by evaporation. The solid material was dried in an oven at 30° C. under reduced pressure overnight to give 6.5 g solid amorphous neutral S-omeprazole.

Examples 2 to 7 inclusive illustrate the preparation of neutral S-omeprazole form A by recrystallization of the amorphous substance prepared in Example 1.

EXAMPLE 2

Amorphous neutral S-omeprazole (0.5 g) was dissolved in ethyl acetate (2g). The solution was placed over night in the refrigerator (−20° C.). Crystals were formed spontaneously. The slurry of crystals obtained was used for seeding in some of the following Examples.

EXAMPLE 3

Amorphous neutral S-omeprazole (2 g) was dissolved in ethyl acetate (20 ml) at room temperature. The solution was seeded with the crystals obtained in Example 2 and allowed to crystallize overnight. The crystals obtained were washed with ethyl acetate (2×2 ml) and dried at +20 C. in air to give 1.3 g of neutral S-omeprazole form A.

EXAMPLE 4

Amorphous neutral S-omeprazole (0.5 g) was dissolved in 2 ml methylene chloride and 4 ml iso-octane was added. The solution was seeded with a small amount of neutral S-omeprazole form A. After 4 days crystals were formed. The substance was filtered off and washed with iso-octane (1 ml) and dried at room temperature.

EXAMPLE 5

Amorphous neutral S-omeprazole (5.0 g ) was dissolved at room temperature in ethyl acetate (40 ml) and a small amount of water (0.5 ml) was added. The solution was seeded with crystalline neutral S-omeprazole form A and cooled to 0° C. The solution was allowed to crystallize overnight at 0° C. The resulting crystals were filtered off, washed with ethyl acetate (3×5 ml) and dried at +40° C. under reduced pressure to give 3.4 g neutral S-omeprazole form A.

EXAMPLE 6

Amorphous neutral S-omeprazole (3 g) was dissolved in toluene (9 ml) at room temperature and ethyl acetate (20 ml) was added. The solution was seeded with neutral S-omeprazole form A and was allowed to crystallize at room temperature for about half an hour. Further ethyl acetate was added ( 9 ml) and the solution was allowed to crystallise overnight. Then the slurry was cooled to 0° C. and allowed to crystallise for 20 hours. The crystals were filtered off, washed with iso-octane (2×5 ml) and dried at +40° C. under reduced pressure giving 2.0 g of neutral S-omeprazole form A.

EXAMPLE 7

Preparation of neutral S-omeprazole form A from an extraction solution in methylene chloride.

Sodium salt of S-omeprazole (20 g) was dissolved in water (200 ml) at room temperature. Methylene chloride (200 ml) was added. The two phase mixture was agitated and aqueous acetic acid (25% v/v, 12.5 ml) was added. The mixture was stirred for 15 minutes and then the phases were allowed to separate. The methylene chloride solution was charged into a round flask and solvent was evaporated until the dilution was 4 ml methylene chloride per gram of S-omeprazole. 18.9 g of this solution, containing 3 g of S-omeprazole, was added to a round flask. Acetontrile was added (50 ml) and the solution was seeded with neutral S-omeprazole form A and left overnight. The methylene chloride was evaporated until 22.5 ml solvent remained. The solution was then allowed to crystallize overnight at room temperature. 15 ml of ethyl acetate was added and the resulting mixture filtered. The crystals were washed with ethyl acetate (3×3 ml) and dried at +40° C. under reduced pressure to give 1.0 g neutral S-omeprazole form A.

EXAMPLE 8
Preparation of neutral S-omeprazole form A by crystallization from a solution of S-omeprazole.

A reaction mixture containing S-omeprazole (1.9 g) in toluene is concentrated by evaporation of toluen until the concentration is 0.71 g/ml toluene. Then ethyl acetate (16 ml) is added to the solution. At room temperature the solution is seeded with 0.2 g neutral S-omeprazole form A and cooled to 0° C. The solution was allowed to crystallize overnight at 0° C. The resulting crystals were filtered off, washed with ethyl acetate (2×4 ml) and dried at 30° C. under reduced pressure to give 0.89 g neutral S-omeprazole, form A.

EXAMPLE 9
Preparation of neutral S-omeprazole form A by re-crystallization.

Partly crystalline S-omeprazole, form A (5.0 g) was dissolved in 258 ml ethyl acetate at 40° C. The solution was cooled to room temperature and the ethyl acetate was slowly evaporated under reduced pressure until 43 ml ethyl acetate remained. At room temperature, the concentrated solution was seeded with neutral S-omeprazole form A. The slurry was then cooled to 0° C. for 5 hours. Then, ethyl acetate (6.7 ml) was added and the resulting slurry filtered. The crystals were re-slurried in 20 ml ethyl acetate, the solvent was filtered off and the crystals dried at 25° C. under reduced pressure to give 2.9 g neutral S-omeprazole form A.

EXAMPLE 10
Preparation of neutral S-omeprazole form B by reaction crystallization from a water/acetone (80/20 % v/v) mixture.

The sodium salt of S-omeprazole (2 g) was dissolved in a mixture of water (16 ml) and acetone (4 ml). Aqueous acetic acid (25 % v/v) was slowly added to the solution in an amount of 0.45 ml which was until the solution had a pH of 10. The resulting slurry was left overnight at room temperature and the cystals were filtered off and washed with water (3×5 ml), dried at +40° C. under reduced pressure giving 0.9 g neutral S-omeprazole form B.

EXAMPLE 11
Preparation of neutral S-omeprazole form B by reaction crystallization from a water/acetone (90/10% v/v) mixture.

The sodium salt of S-omeprazole (5.2 g) was dissolved in water (46.9 ml). Acetone (5.2 ml) was added to the solution. Under vigorous stirring, 3.2 ml of aqueous acetic acid (25% v/v) was slowly added. Crystallization started when the pH reached 10. At the end of the addition the pH was 7. After 3 hours the crystals were filtered off and washed with water (3×5 ml). The crystals were dried at 40° C. under reduced pressure over night to give 4.4 g partly crystalline neutral S-omeprazole form B.

What is claimed is:

1. S-Omeprazole in a neutral form, wherein it is in a partly crystalline state.

2. S-Omeprazole according to claim 1, wherein it is in a substantially crystalline state.

3. S-omeprazole according to claim 1 or 2, wherein it is in form A.

4. S-omeprazole according to claim 1 or 2, wherein it is in form B.

5. A process for preparing S-omeprazole according to claim 1 or 3 which comprises crystallizing the S-omeprazole from a solution comprising neutral S-omeprazole in one or more organic solvents and optionally water.

6. The process according to claim 5, wherein the solution of neutral S-omeprazole is formed by dissolving S-omeprazole in the organic solvent.

7. The process according to claim 5, wherein the organic solvent is ethyl acetate or acetonitrile.

8. The process according to claim 5, wherein the solution of neutral S-omeprazole is formed from a chemical reaction solution comprising S-omeprazole in an organic solvent.

9. The process according to claim 5, wherein the solution of neutral S-omeprazole is formed from an extraction phase comprising S-omeprazole in an organic solvent.

10. The process according to claim 8 or 9, wherein the organic solvent is methylene chloride or toluene.

11. The process according to claim 10, wherein crystallization is induced by adding a precipitating solvent.

12. A process for preparing S-omeprazole according to claim 1 or 3 which comprises precipitating the S-omeprazole from a solution comprising an alkaline salt of S-omeprazole in water and, optionally one or more organic solvents, by adding an acid to the solution.

13. The process according to claim 12, wherein the alkaline salt of S-omeprazole is dissolved in a mixture of water and an organic solvent.

14. A process according to claim 12, wherein the pH of the solution after the addition of the acid is between 7 and 10.

15. A pharmaceutical composition comprising S-omeprazole according to any one of claims 1, 3, 4 or 5 as active ingredient in association with a pharmaceutically acceptable carrier.

16. A method of treating a gastric-acid related condition which comprises administering to a patient in need of such treatment a therapeutically effective amount of S-omeprazole according to any one of claims 1, 2, 3 or 4.

17. The process according to claim 11, wherein the precipitating solvent is selected from the group consisting of isooctane, acetronitrile or ethyl acetate.

* * * * *

UNITED STATES PATENT AND TRADEMARK OFFICE
CERTIFICATE OF CORRECTION

PATENT NO.   : 6,162,816
DATED        : December 19, 2000
INVENTOR(S)  : Bohlin et al.

It is certified that error appears in the above-identified patent and that said Letters Patent is hereby corrected as shown below:

Column 8, claim 5,
Line 14, delete "claim 1 or 3" and substitute therefor -- claim 1 or 2 --.

Column 8, claim 12,
Line 33, delete "claim 1 or 3" and substitute therefor -- claim 1 or 2 --.

Column 8, claim 15,
Line 43, delete "claims 1, 3, 4 or 5" and substitute therefor -- claims 1, 2, 3, or 4 --.

Signed and Sealed this

Twentieth Day of November, 2001

*Attest:*

*Attesting Officer*

NICHOLAS P. GODICI
*Acting Director of the United States Patent and Trademark Office*